United States Patent [19]

Holly

[11] Patent Number: 4,597,965
[45] Date of Patent: Jul. 1, 1986

[54] METHOD AND COMPOSITION FOR CONTROLLING CORNEAL HYDRATION

[75] Inventor: Frank J. Holly, Lubbock, Tex.

[73] Assignee: Holles Laboratories, Inc., Cohasset, Mass.

[21] Appl. No.: 382,249

[22] Filed: May 26, 1982

Related U.S. Application Data

[60] Continuation of Ser. No. 227,819, Jan. 23, 1981, abandoned, which is a division of Ser. No. 46,188, Jun. 7, 1979, Pat. No. 4,271,144.

[51] Int. Cl.⁴ .............................................. A61K 31/78
[52] U.S. Cl. ........................................ 424/81; 514/912
[58] Field of Search ................ 424/81, 180, 310, 326

[56] References Cited

U.S. PATENT DOCUMENTS

| | | | |
|---|---|---|---|
| 2,547,653 | 4/1951 | Minnis et al. | 424/180 |
| 3,843,782 | 10/1974 | Kzezanoski et al. | 424/78 |
| 3,920,810 | 11/1975 | Rankin | 424/80 |
| 3,935,303 | 1/1976 | Khromov et al. | 424/78 |
| 3,978,201 | 8/1976 | Khromov et al. | 424/81 |
| 4,003,991 | 1/1977 | Khromov et al. | 424/81 |
| 4,039,662 | 8/1977 | Hecht et al. | 424/180 |

FOREIGN PATENT DOCUMENTS

| | | | |
|---|---|---|---|
| 2526998 | 1/1977 | Fed. Rep. of Germany | 424/81 |
| 2333500 | 1/1977 | France | |
| 1414182 | 11/1975 | United Kingdom | 424/81 |

OTHER PUBLICATIONS

Chem. Abst. 79, 73707(b) (1973)–Arnaud et al.
Chem. Abst. 87, 157,125(p) (1977)–Khristenko et al.
Chem. Abst. 87, 98,182(e) (1977)–Bellhorn et al.

Primary Examiner—Douglas W. Robinson
Attorney, Agent, or Firm—Robert L. Goldberg

[57] ABSTRACT

An ophthalmic solution for treating corneal edema concurrent with epithelial discontinuity, healing epithelial defects, and protecting against epithelial trauma containing electrolytes at only isotonic levels but containing hydrophilic macromolecules at such concentration that their collodial osmotic pressure is equal or greater than the imbibition pressure of corneal stroma.

5 Claims, No Drawings

METHOD AND COMPOSITION FOR CONTROLLING CORNEAL HYDRATION

This is a continuation of application Ser. No. 227,819, filed Jan. 23, 1981, now abandoned, which is a division of Ser. No. 06/046,188, filed 6-7-79, now U.S. Pat. No. 4,271,144.

BACKGROUND OF THE INVENTION

1. Field of the Invention

The present invention relates to a multifunctional aqueous ophthalmic preparation that is designed to be used topically in the eyes of humans and domestic animals. The present invention further relates to the provision of an aqueous solution of physiological pH, having hyperosmolality with respect to corneal stroma of the colloidal components only, which is useful for dehydrating edematous cornea even in the presence of damaged corneal epithelium when the barrier properties to small molecular weight electrolytes of the epithelial layer is lost. The invention also relates to an ophthalmic agent that is beneficial in promoting the permanent healing of epithelial defects. Still further, the invention relates to a solution that is capable of protecting the corneal epithelium from injury such as abrasion that may result from close and prolonged contact with solid surfaces, such as in the diagnostic procedures of tonography and tonometry, or any other procedure where a foreign solid object is brought in close contact with the preocular surface. Furthermore, the invention relates to an ophthalmic solution that can be used for irrigating purposes during prolonged intraocular surgical operations, e.g. vitrectomy, to preserve corneal thickness and clarity and to protect the cellular interfaces so that the incidence and the severity of postoperative complications involving the corneal epithelium or endothelium can be prevented. The invention also relates to the attainment of all the foregoing with significant decrease of ocular discomfort if present, and without optical interference with visual acuity. The invention further relates to an ophthalmic solution that can be formulated to have bactericidal activity without detectable decrease in its therapeutic efficacy.

2. Description of the Prior Art

The most powerful refractive medium of the eye, the cornea has to be transparent and must have an optically smooth surface to fulfill its function, the formation of a sharp visual image on the retina. The cornea is a normally transparent, mostly acellular connective tissue consisting of collagen fibers and mucopolysaccharides. This tissue is called the stroma, which is covered by several layers of epithelial cells on the exterior surface, while its interior surface is covered with a single layer of endothelial cells. The macromolecules of the stroma form a loosely connected matrix that contains about 80% by weight of aqueous fluid. This interstitial fluid of the stroma is nearly isotonic. The tissue, however, behaves as if it were somewhat dehydrated, since it tends to imbibe, i.e. absorb, additional fluid when immersed in physiological saline. This occurs because the additional osmolality of its macromolecular matrix causes a net flow of water into the stroma by osmosis, with the epithelium acting as a semipermeable membrane. Osmolality is a property of a solution which depends on the concentration of the solute molecules per unit weight of solvent and determines the amount of solvent absorbed by a particular substrate, usually in the presence of a semipermeable membrane. This tendency of water absorption is measured in terms of the so-called "imbibition pressure", which is about 40–60 torrs for the normal cornea. As the degree of hydration of the stroma increases, the imbibition pressure diminishes. Active transport of electrolytes and thus water out of the stroma by its boundary layers of cells keeps the stromal hydration at its normal, i.e. somewhat dehydrated, level in order to maintain its transparency. As the cornea imbibes water, it becomes progressively more cloudy diminishing visual acuity. A highly edematous cornea scatters so much light that it appears to be quite opaque.

The superficial epithelium can also become edematous. In such a case, droplets of fluid accumulate in the dilated intercellular spaces of the epithelium. Edematous epithelial tissue can loose its integrity; the cellular adhesiveness is lowered to such a degree that it can easily be abraded.

Corneal edema can result from various causes. A malfunction of the corneal endothelium usually results in severe corneal edema. Traumatized corneal epithelium, recurrent epithelial erosion, and epithelial discontinuities of other types can also result in corneal edema drastically reducing visual acuity.

Heretofore, corneal edema of sufficient severity to result in blurred vision has been treated with hypertonic salt solutions i.e. solutions which cause water to flow out of the cornea by having a higher tonicity than the solution within the cornea. Aqueous solutions of sodium chloride at concentrations of 2% and 5% by weight, instilled several times a day may provide symptomatic relief and thus temporarily restore visual acuity. Hydrogel lenses have also been used in conjunctin with hypertonic salt solutions and have been able to prolong the dehydrating effect of the hypertonic salt solution somewhat.

In addition to hypertonic sodium chloride solutions, hyperosmotic ointments containing 40% glucose are also employed in clinical practice, but its dehydrating effect is only slightly higher than that of the 5% sodium chloride solution. Hyperosmotic compositions are those containing a higher concentration of osmotically active components than that contained within a physiological salt solution containing 0.9% by weight of sodium chloride. Anhydrous glycerol is a highly effective dehydrating agent, but it is poorly tolerated by the eye of most patients as indicated by considerable discomfort, conjunctival injection, and photophobia, i.e. an abnormal visual intolerance of light.

All the foregoing hyperosmotic preparations have one weakness in common. They only have the desired dehydrating effect on the cornea, if the epithelium, which acts as an imperfect semipermeable membrane, is intact, since osmotic effects can occur only across a membrane that excludes at least one of the solutes. Hence, in many patients having corneal edema which is associated with epithelium of poor integrity, i.e. having epithelial discontinuities, the symptomatic treatment with hypertonic salt solutions or glucose ointment is ineffective, and may even be harmful, as the solute can readily penetrate the stroma achieving hypertonic levels inside the tissue which causes further imbibition of water with the resulting clouding of the cornea which diminishes visual acuity. Even in the presence of intact epithelium, the effect of hypertonic salt solutions is short-lived, as the drops are diluted and the excess salt is washed out of the eye by reflex tearing.

Some attempts have been made to improve the observed poor performance of hypertonic salt solutions especially in cases of corneal edema concurrent with epithelial discontinuity. Artificial tears containing "mucomimetic" polymers, i.e. polymers which mimic the action of naturally-occurring mucin which acts as a wetting agent in the eye and thus is responsible for tear film stability, have been used as ophthalmic vehicles for sodium chloride at hypertonic levels. However, in these polymeric solutions the osmolality of the dissolved polymers is negligibly small, and thus these attempts have added little to the performance of the hypertonic solutions other than lessening the discomfort upon application.

It is accordingly an object of the present invention to include colloidal components in the ophthalmic formulations at sufficiently high concentration so that their osmotic pressure is equivalent to or supercedes the imbibition pressure of a deturgescent cornea. The colloidal components have to be of such molecular size and shape that they cannot penetrate readily even the denuded stroma. The colloidal substance used also has to be sufficiently water-soluble and of low viscosity so that the required high solution concentration can be achieved before the limit of solubility is reached and without the high concentrations resulting in impractically high viscosity. A further object of the present invention is the provision of such solution with colloidal hyperosmolality where the hydrophilic polymers included readily adsorb at the cellular and tissue interfaces thereby prolonging the beneficial osmotic effect. It is also an object of this invention that the polymer layer adsorbed at the bio-interfaces should exert a beneficial effect on the healing of epithelium, on the adhesion of regenerating epithelium to the stroma and provide protection for the corneal epithelium against mechanical abrasion and other trauma besides prolonging the dehydrating osmotic effect for edematous corneas.

SUMMARY OF THE INVENTION

These and still other objectives, as will become apparent from the following disclosure, are attained by the composition of the present invention, which in its broadest term comprises a hydrophilic, high molecular weight polymer dissolved in isotonic aqueous electrolyte solution at sufficiently high concentration to effect a colloidal osmotic pressure equal to or greater than that of a deturgescent cornea, i.e. between about 40 and about 200 millimeters of mercury. Highly water-soluble polysaccharides or polyamides with an average molecular weight ranging from about 20,000 to about 150,000 daltons are preferred that can effect the osmotic pressure desired at solution concentrations ranging from 5% to 25%, that have the hydrophilicity, adsorptivity, and low viscosity even at high solution concentrations that are required to achieve the desirable effects. These substances are also nontoxic and are highly compatible with the macromolecular tear components, the intercellular adhesive of the epithelium, and the glycosaminoglycans that form the ground substance of the stroma.

DETAILED DESCRIPTION OF THE INVENTION

A preferred colloidal component for use in the ophthalmic solution of the present invention is dextran, a polymer of glucose that is chiefly joined through $\alpha$-1,6-glycosidic linkages, and is obtained by appropriate processing of the high molecular weight product derived from the fermentation of sucrose by the bacteria *Leuconostoc mesenteroides*. The ophthalmic solution component has an average molecular weight of at least about 40,000 and not more than about 150,000 daltons, and is obtained by partial hydrolysis and fractionation of the high molecular weight fermentation product. This polysaccharide is highly water-soluble forming aqueous solutions of low viscosity, it carries no net electric charge, and its effect on water surface tension is negligible. Another preferred hydrophilic polymer useful as the colloidal component of the ophthalmic solution of the present invention is the synthetic polymer poly (acrylamide) having an average molecular weight between about 20,000 and about 150,000 daltons. This polymer is also highly water-soluble forming aqueous solutions of low viscosity, the molecule carries no net electric charge and it has a negligible effect on water surface tension. The respective techniques of producing these polymers are well established and form no part of the present invention.

Various molecular weight dextrans are described in U.S. Pat. No. 4,039,662 as being useful in preparing artificial tear solutions when used in combination with benzalkonium chloride. U.S. Pat. No. 3,920,810 describes polyacrylamide containing ophthalmic solutions as artificial tear solutions. In addition to using these ophthalmic solutions as artificial tear materials, they are also suggested as being useful as lubricating and cushioning agents for the eye after an injury or surgery, or as cleaning, lubricating, and cushioning agent for hard and gel type contact lens. However, neither patent teaches nor suggests the desirability of preparing a solution of such a polymer at a concentration sufficient to produce a solution having a colloidal osmolality equal to or exceeding the collodial osmolality of a deturgescent cornea. Furthermore, neither patent teaches nor suggests the beneficial effects resulting from controlling corneal hydration by the use of such a solution in the eye as described herein. The factors influencing corneal hydraton are discussed in *Investigative Ophthalmology*, Vol. 1, No. 2, pp 151-157 (1962) by J. E. Harris. While that article discusses corneal hydration in general and the desirability of dehydrating the cornea in certain instances, only two materials are discussed for use in the eye. The first was a 25% solution of scrum albumin which had the disadvantages of being somewhat toxic to the epithelium, as well as being rapidly lost from the conjunctival sac. The second was a 5% solution of a low viscosity carboxymethylcellulose sodium salt having a molecular weight of about 40,000, which was said to have some merit in cases where the stroma could be acted on directly but was of no value when the epithelial tissue was still partially intact, e.g. bulious keratopathy or epithelial edema, probably due to its ionic nature, sodium ion content, the comparatively high viscosity of carboxymethylcellulose as opposed to the polymers of the present invention, and the relatively low concentration of polymer used. While dextran is mentioned therein as having been used in vitro on excised pieces of cornea, there is no indication of its use in the eye nor of the exact molecular weight of the polymer which was used.

Aqueous solutions of dextran and poly(acrylamide) are highly stable and are compatible with the biopolymers found in tears. Both polymers also have very low toxicity. Since these polymers are nonionic, the concentration of inorganic salts needed to achieve physiological tonicity has no appreciable deleterious effect on their solubility so that polymer solutions at concentration levels needed to achieve and even surpass the colloidal osmolality of the deturgescent cornea can readily be formulated even in the presence of inorganic electrolytes.

It is preferred that the ophthalmic solution of the present invention be isotonic. Any of the salts described as useful in the prior art for rendering an ophthalmic solution isotonic may be used in the present invention, such as, for example, sodium chloride, potassium chloride, calcium chloride, magnesium chloride, and various sulfates, phosphates, borates, nitrates, citrates, acetates, etc.

If desired, it is also possible to add a preservative to the ophthalmic solution used in the present invention. For example, biocides such as benzalkonium chloride, thimerosal, phenylmercuric nitrate, chlorobutanol, methyl paraben, propyl paraben, chlorhexidine digluconate, and sorbic acid and chelating agents, such as for example, di, tri, or tetrasodium ethylene diamine tetraacetate, also known as edetates, may be added at concentrations between about 0.001% and 0.1% by weight.

In addition, the composition of the present invention can also contain as an optional ingredient an eye compatible anesthetic such as, for example, benoxinate, butyl-4-amino-benzoate, naepaine, and phenacaine. A preferred anesthetic is proparacaine.

Furthermore, the composition of the present invention may also be used as a carrier for ophthalmic medicants, for example: mydriatics such as tropicamide, atropine, and epinephrine; miotics such as pilocarpine and carbachol; cycloplegics such as cyclopentolate; anti-inflammatories such as dexamethasone and prednisolone; anti-infectives such as sulfas and antibiotics; and vasoconstrictors such as phenylephrine and naphazoline. The medicants may be present in the form of their pharmaceutically acceptable salts or esters.

Another optional ingredient of the composition of the present invention is an eye compatible fluorescing compound of the type used in fluorophotometric determinations such as that used when fitting contact lens. Examples of such fluorescing compounds include sodium fluorescein, with a preferred fluorescing compound being fluorexon.

The dehydrating solution of the present invention, a concentrated aqueous solution of certain hydrophilic colloids, is useful in a number of contexts. Primary among these is the intensive dehydrating effect on edematous cornea even in the complete absence of epithelium, which quickly results in improved visual acuity. The solution also exerts a hydrating effect of edematous epithelium of poor integrity removing the intercellular pools of fluid accumulated in the epithelium and thereby increasing the cell to cell and the cell to substrate (basement membrane) adhesion. A related effect is the lessening or even complete disapperance of the occasional severe discomfort experienced by patients with damaged corneal epithelium.

While not wishing to be bound by theory, it is believed that the beneficial effect of the macromolecular dehydrating component contained in the ophthamlic solution of this invention appears to be manifested by both bulk and interfacial means. There are indications that despite their low surface activity and lack of electric charge, certain hydrophilic polymers, such as the ones described herein, adsorb at the cellular and tissue boundaries and the observed beneficial effect on stromal hydratic epithelial healing, and epithelial adhesion is at least partly due to the presence of this adsorbed macromolecular layer which forms an osmotic gradient at the cornea-tear interface. Other hydrophilic polymers, although similar in molecular weight and solubility, fail to produce the desired effect in vivo, and it is believed that such failure is due to the failure of such solutions to form an osmotic gradient at the cornea-tear interface.

The attainment of the objectives of formulating an ophthalmic solution that can be used to manage corneal edema in the presence of injured or absent epithelium and thereby restore and preserve visual acuity, to protect corneal epithelium from injury resulting from mechanical or chemical trauma or manipulation during surgical interventions, and to promote the proliferation and attachment of corneal epithelium thereby avoiding subsequent complications, is illustrated by the following examples, which are intended to be purely exemplary of the use of the invention.

EXAMPLE I

Dextran-40 polymer having an average molecular weight of about 40,000 daltons and sodium choride are dissolved in distilled water in the following proportions:

| Dextran-40 | 6.00 grams |
| Sodium chloride | 0.90 grams |
| Distilled water | 93.1 milliliters |

The colloidal osmolality of such a solution is about 3 mOsm, which corresponds to an osmotic pressure of 57 mm Hg. The solution can be readily heat-sterilized since the polymer dextran remains in solution even at elevated temperatures. The effectiveness of this solution in controlling corneal hydration in the complete absence of epithelium was compared to a hypertonic salt solution containing sodium chloride at 5% concentration level in the following experiment:

The corneal epithelium was removed by chemical and mechanical means from both eyes of 15 rabbits. The solution was topically applied to the eyes at every two hours seven times a day. One eye received the dextran solution, the other eye was treated with the 5% sodium chloride solution. The thickness of the cornea in each eye was determined by pachometry prior to the removal of the epithelium and once every day during the healing period. Pachometry is an optical method utilizing a slit beam of light that is reflected from the anterior and posterior surface of the cornea and is capable of determing corneal thickness to the accuracy of ±0.01 mm. The average corneal thickness for each group during the first six days of the study is shown in Table I.

| | Average corneal thickness ± S.D. in mm. | |
| --- | --- | --- |
| Healing time (days) | Dextran solution | Hypertonic salt sol'n. |
| 0 | 0.42 ± .01 | 0.41 ± .01 |
| 1 | 0.53 ± .02 | 0.65 ± .01 |
| 2 | 0.58 ± .01 | 0.68 ± .02 |
| 3 | 0.61 ± .03 | 0.71 ± .04 |
| 4 | 0.60 ± .02 | 0.72 ± .02 |
| 5 | 0.52 ± .03 | 0.72 ± .03 |

Purposely, the epithelial removal was extensive involving the limbus so that no complete healing occurred during the first 5 days of treatment.

EXAMPLE II

The following composition was tested against a commercial hypertonic solution containing 5% sodium chloride in a polymer base (Adsorbonac-5%, sold by Burton, Parsons, and Co., of Washington, D.C.):

| | |
|---|---|
| Dextran-70 | 9.00 grams |
| Sodium chloride | 0.90 grams |
| Benzalkonium chloride | 0.004 grams |
| Disodium edetate | 0.01 grams |
| Distilled water | 90.10 milliliters |

Forty rabbit eyes were deepithelialized but less extensively than in Example I. Half of the eyes were treated with the dextran solution, the other half were treated with the commercial hypertonic solution seven times daily. The corneal thickness was determined daily and after 5 days, the number of eyes completely healed were determined. The results are shown in Table II:

| | Average corneal thickness ± S.D. in mm. | |
|---|---|---|
| Days of Treatment | Dextran solution | Hypertonic salt sol'n |
| 0 | 0.40 ± .01 | 0.41 ± .01 |
| 1 | 0.62 ± .02 | 0.73 ± .02 |
| 2 | 0.63 ± .01 | 0.74 ± .01 |
| 3 | 0.60 ± .01 | 0.72 ± .01 |
| 4 | 0.58 ± .03 | 0.73 ± .01 |
| 5 | 0.55 ± .04 | 0.71 ± .03 |
| No. of eyes healed: | 10 (50%) | 5 (25%) |

EXAMPLE III

Forty rabbit eyes were burned with ultraviolet radiation on day 0 and on day 2. Ten eyes were treated with the following solution:

| | |
|---|---|
| Dextran-40 | 6.00 grams |
| Sodium chloride | 0.90 grams |
| Distilled water | 93.1 milliliters |

Another ten eyes were treated with the following solution:

| | |
|---|---|
| Poly(vinyl pyrrolidone) M.W. = 40,000 daltons | 6.00 grams |
| Sodium chloride | 0.90 grams |
| Distilled water | 93.1 milliliters |

Ten eyes were treated with 0.90% sodium chloride and other ten eyes were treated with 5% sodium chloride solution at every 2 hours seven times a day. Corneal thickness was measured daily and the condition of the epithelium was graded on a subjective scale from 0 to 4+ after staining with Rose Bengal stain. The results are shown in Table III:

| Treatment | Average corneal thickness (mm)/grade of epithelium | | | |
|---|---|---|---|---|
| Days | Dextran | Polyvinylpyrr | 0.9% NaCl | 5% NaCl |
| 0 | 0.40/0.0 | 0.41/0.0 | 0.39/0.0 | 0.40/0.0 |
| 1 | 0.48/1.2 | 0.56/1.5 | 0.59/2.1 | 0.60/2.5 |
| 2 | 0.52/0.9 | 0.60/2.0 | 0.61/2.0 | 0.62/2.3 |
| 3 | 0.54/1.4 | 0.62/2.3 | 0.66/2.7 | 0.64/3.3 |
| 4 | 0.50/1.0 | 0.61/2.1 | 0.64/2.5 | 0.65/3.0 |
| 5 | 0.47/0.5 | 0.58/1.6 | 0.63/2.0 | 0.64/2.8 |

EXAMPLE IV

6% Dextran-40 solution in isotonic saline preserved with benzalkonium chloride solution in the presence of disodium edetate was used on twenty patients undergoing tonography. In this procedure, a cylindrical solid is pressed against the cornea, which is topically anesthetized, for seven minutes. Damage to the epithelium always occurs partially due to the application of the anesthetic and partially from the mechanical trauma resulting from the prolonged contact of the cornea with a solid foreign body. Punctate staining of the epithelium with fluorescein and moderate corneal edema are routinely observed in patients undergoing tonometry and these effects can last up to 48 hours. The dextran solution was applied to various groups of patients;

/A/ prior to the application of the anesthetic
/B/ after anesthesia but prior to tonography
/C/ after tonography The cornea was stained with fluorescein immediately (I) and two hours (II) after tonography. At this time the degree of stromal haziness, an indication of the degree of edema, was also observed. The results are shown in Table IV:

| | FLUORESCEIN STAINING | | STROMAL HAZE |
|---|---|---|---|
| GROUP | I. | II. | II. |
| A | negligible | absent | absent |
| B | moderate | negligible | absent |
| C | considerable | moderate | absent |
| Control* | considerable | considerable | present |

*isotonic saline was used in place of dextran solution.

EXAMPLE V

10% Dextran-70 solution in isotonic saline was used to irrigate the preocular surface of patients undergoing intraocular surgery such as vitretomy or intraocular lens implant. The same solution but containing preservatives was used topically seven times daily as postoperative treatment on patients for two weeks following surgery. A significant reduction in corneal complications for the patients treated with this solution was observed when compared to those receiving only conventional management.

EXAMPLE VI

Polyacrylamide polymer having an average molecular weight of about 40,000 daltons and sodium chloride were dissolved in distilled water in the following proportions:

| | |
|---|---|
| Polyacrylamide | 6.00 grams |
| Sodium chloride | 0.90 grams |
| Distilled water | 93.1 milliliters |

This solution was tested in accordance with the procedure of Example I, above, with favorable results. Solutions prepared from polyacrylamide were also employed in treating corneal edema and epithelial discontinuities in patients as well as a postoperative treatment after surgery involving the cornea both in Mexico and in Europe with promising results.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method of corneal dehydration in a human or animal eye comprising applying thereto an effective cornea dehydrating amount of an aqueous solution of a hydrophilic nonviscous polyacrylamide having an average molecular weight of between about 40,000 and about 150,000, said polyacrylamide being present at a colloidal osmolality between about 40 and 200 torr and in a concentration of from about 5 to 25% by weight.

2. The method of claim 1, in which said ophthalmic solution comprises, in addition, an eye compatible preservative.

3. The method of claim 2 in which said preservative is chlorhexidine digluconate.

4. The method of claim 1 in which said ophthalmic solution comprises, in addition, an eye compatible anesthetic.

5. The method of claim 4 in which said anesthetic is proparacaine.